US012678131B2

(12) United States Patent (10) Patent No.: US 12,678,131 B2
Koshino (45) Date of Patent: Jul. 14, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riko Koshino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 56 days.

(21) Appl. No.: 18/463,218

(22) Filed: Sep. 7, 2023

(65) Prior Publication Data

US 2023/0414197 A1 Dec. 28, 2023

Related U.S. Application Data

(63) Continuation of application No. PCT/JP2022/003772, filed on Feb. 1, 2022.

(30) Foreign Application Priority Data

Mar. 8, 2021 (JP) ................................. 2021-036170

(51) Int. Cl.
*A61B 8/00* (2006.01)
(52) U.S. Cl.
CPC ............ *A61B 8/406* (2013.01); *A61B 8/4245* (2013.01); *A61B 8/4488* (2013.01); *A61B 8/461* (2013.01); *A61B 8/5238* (2013.01)
(58) Field of Classification Search
CPC ..... A61B 8/0825; A61B 8/406; A61B 8/4245; A61B 8/4488; A61B 8/461; A61B 8/5238
See application file for complete search history.

(56) References Cited

U.S. PATENT DOCUMENTS

| | | | |
|---|---|---|---|
| 2002/0167549 A1 | 11/2002 | Cupples et al. | |
| 2008/0058611 A1 | 3/2008 | Tsubura | |
| 2013/0290826 A1 | 10/2013 | Niwa et al. | |
| 2015/0146855 A1 | 5/2015 | Futamura | |
| 2018/0000453 A1 | 1/2018 | Hunter et al. | |

(Continued)

FOREIGN PATENT DOCUMENTS

| | | |
|---|---|---|
| JP | 2008-059071 A | 3/2008 |
| JP | 2013-132514 A | 7/2013 |

(Continued)

OTHER PUBLICATIONS

International Search Report issued in PCT/JP2022/003772; mailed Apr. 26, 2022.

(Continued)

*Primary Examiner* — Brooke Lyn Klein
(74) *Attorney, Agent, or Firm* — Studebaker Brackett PLLC

(57) ABSTRACT

An ultrasound diagnostic apparatus and a control method of an ultrasound diagnostic apparatus that enable a user to easily use information stored in a tag of an ultrasound image are provided. An ultrasound diagnostic apparatus (1) displays an ultrasound image on which a breast schema image showing a position of an ultrasound probe (2) in imaging is superimposed, and includes a text information conversion unit (17) that converts the position of the ultrasound probe (2) plotted on the breast schema image into text information, and a text information storage unit (18) that stores the text information converted by the text information conversion unit (17) in a tag attached to the ultrasound image.

2 Claims, 7 Drawing Sheets

(56)       References Cited

U.S. PATENT DOCUMENTS

| | | | |
|---|---|---|---|
| 2018/0220994 A1 | 8/2018 | Sugiyama | |
| 2018/0360427 A1 | 12/2018 | Nakano et al. | |
| 2020/0294226 A1 | 9/2020 | Fujihara et al. | |
| 2021/0030392 A1 | 2/2021 | Dmitrieva et al. | |

FOREIGN PATENT DOCUMENTS

| | | | |
|---|---|---|---|
| JP | 2017-099769 A | 6/2017 |
| JP | 2017-225850 A | 12/2017 |
| JP | 2019-517345 A | 6/2019 |
| JP | 2020-146074 A | 9/2020 |

OTHER PUBLICATIONS

International Preliminary Report On Patentability (Chapter I) and Written Opinion of the International Searching Authority issued in PCT/JP2022/003772; issued Sep. 12, 2023.

The extended European search report issued by the European Patent Office on Jul. 2, 2024, which corresponds to European Patent Application No. 22766678.1-1122 and is related to U.S. Appl. No. 18/463,218.

An Office Action mailed by the Japanese Patent Office on May 19, 2026, which corresponds to Japanese Patent Application No. 2023-505207 and is related to U.S. Appl. No. 18/463,218.

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/003772 filed on Feb. 1, 2022, which claims priority under 35 U.S.C. § 119(a) to Japanese Patent Application No. 2021-036170 filed on Mar. 8, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of an ultrasound diagnostic apparatus used for examining a breast of a subject.

2. Description of the Related Art

In the related art, an ultrasound image representing a tomogram of a subject has been captured using an ultrasound diagnostic apparatus, and a user such as a doctor has diagnosed the subject based on the captured ultrasound image. For example, the technology disclosed in JP2013-132514A has been developed so that the user such as a doctor can smoothly perform the diagnosis. In order for the user such as a doctor to be capable of easily perceiving a location suspected to be abnormal by checking the ultrasound image, JP2013-132514A discloses causing an examiner to assign image information indicating the location suspected to be abnormal to the ultrasound image and storing the assigned image information in a tag of the ultrasound image.

SUMMARY OF THE INVENTION

In the technology of JP2013-132514A, displaying the image information stored in the tag of the ultrasound image on a display device or the like enables the user to visually easily perceive the location suspected to be abnormal. However, reading a meaning of the image information via mechanical processing requires certain processing in addition to processing of reading out the image information. Thus, there is room for improvement in the technology of JP2013-132514A in terms of easily using the information stored in the tag of the ultrasound image.

The present invention has been conceived to eliminate the problem of the related art, and an object thereof is to provide an ultrasound diagnostic apparatus and a control method of an ultrasound diagnostic apparatus that enable a user to easily use information stored in a tag of an ultrasound image.

In order to achieve the object, an ultrasound diagnostic apparatus according to an aspect of the present invention is an ultrasound diagnostic apparatus that displays an ultrasound image on which a breast schema image showing a position of an ultrasound probe in imaging is superimposed, the apparatus comprising a text information conversion unit that converts the position of the ultrasound probe plotted on the breast schema image into text information, and a text information storage unit that stores the text information converted by the text information conversion unit in a tag attached to the ultrasound image.

The ultrasound diagnostic apparatus may further comprise an input device with which a user performs an input operation, in which the text information conversion unit converts the position of the ultrasound probe into the text information based on a position of a plotted point in a case where the user plots the position of the ultrasound probe on the breast schema image by operating the input device.

In this case, the text information conversion unit may convert a region to which the plotted point belongs among a plurality of divided regions of a breast into the text information as the position of the ultrasound probe.

In addition, the text information conversion unit may recognize the position of the ultrasound probe plotted on the breast schema image by analyzing the breast schema image superimposed on the ultrasound image and convert the recognized position of the ultrasound probe into the text information.

In this case, the text information conversion unit may extract a probe mark representing the position of the ultrasound probe from the breast schema image by calculating a difference between the breast schema image and a template of a breast schema and convert a region to which the probe mark belongs among a plurality of divided regions of a breast into the text information as the position of the ultrasound probe.

A control method of an ultrasound diagnostic apparatus according to another aspect of the present invention is a control method of an ultrasound diagnostic apparatus that displays an ultrasound image on which a breast schema image showing a position of an ultrasound probe in imaging is superimposed, the method comprising converting the position of the ultrasound probe plotted on the breast schema image into text information, and storing the converted text information in a tag attached to the ultrasound image.

In the control method of the ultrasound diagnostic apparatus, the position of the ultrasound probe may be converted into the text information based on a position of a plotted point in a case where a user plots the position of the ultrasound probe on the breast schema image superimposed on the ultrasound image.

In this case, a region to which the plotted point belongs among a plurality of divided regions of a breast may be converted into the text information as the position of the ultrasound probe.

In addition, in the control method of the ultrasound diagnostic apparatus, the position of the ultrasound probe plotted on the breast schema image may be recognized by analyzing the breast schema image superimposed on the ultrasound image, and the recognized position of the ultrasound probe may be converted into the text information.

In this case, a probe mark representing the position of the ultrasound probe may be extracted from the breast schema image by calculating a difference between the breast schema image and a template of a breast schema, and a region to which the probe mark belongs among a plurality of divided regions of a breast may be converted into the text information as the position of the ultrasound probe.

According to the present invention, a text information conversion unit that converts a position of an ultrasound probe plotted on a breast schema image into text information, and a text information storage unit that stores the text information converted by the text information conversion unit in a tag attached to an ultrasound image are provided. Thus, a user can easily use information stored in the tag of the ultrasound image.

DESCRIPTION OF THE PREFERRED EMBODIMENTS

Hereinafter, embodiments of the invention will be described with reference to the accompanying drawings.

The description of configuration requirements described below is provided based on the representative embodiment of the present invention, but the present invention is not limited to such an embodiment.

In the present specification, a numerical range represented using "to" means a range including the numerical values before and after "to" as a lower limit value and an upper limit value.

In the present specification, the terms "identical" and "same" include an error range generally allowed in the technical field.

Embodiment 1

Figure 1:
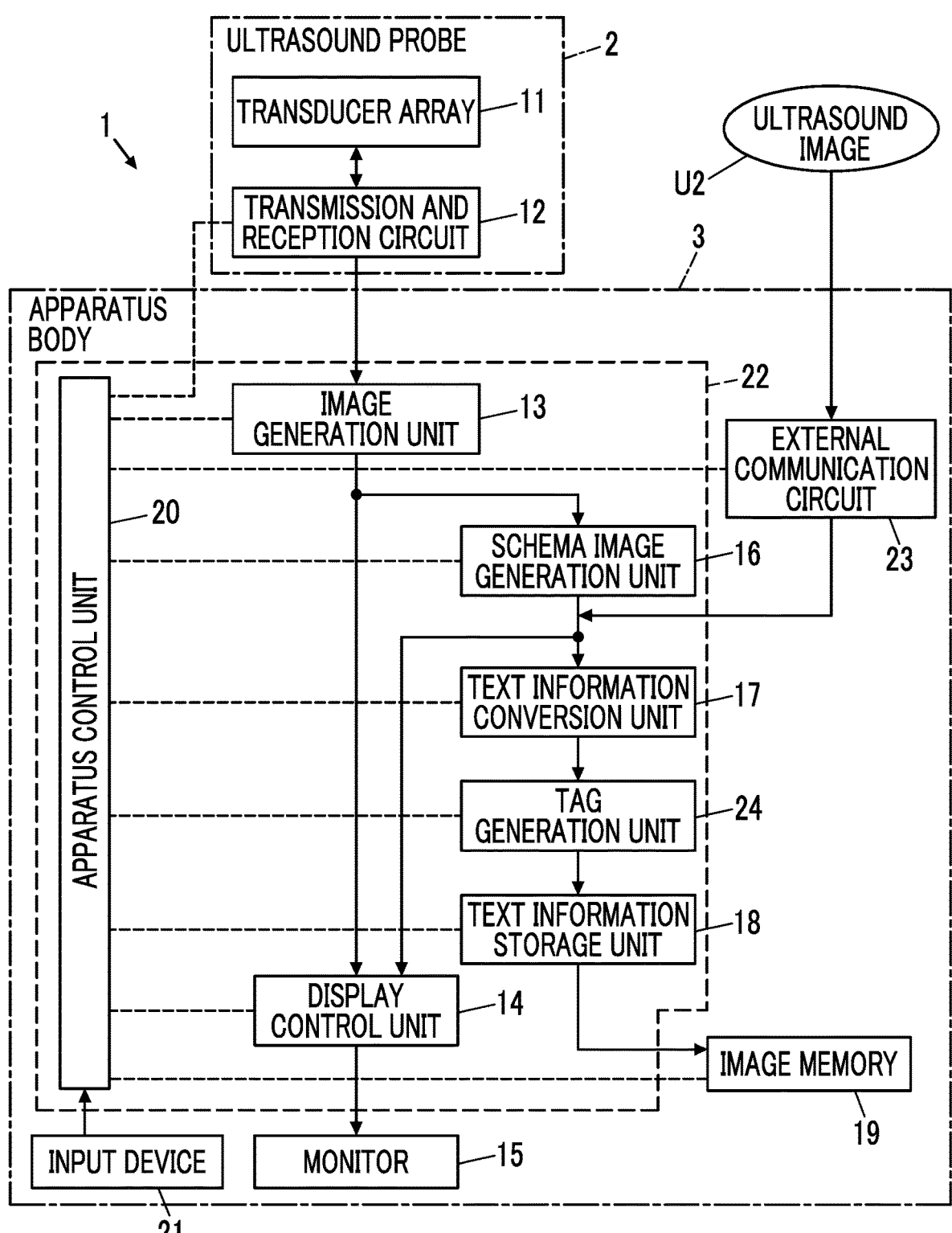
FIG. 1 is a block diagram illustrating a configuration of an ultrasound diagnostic apparatus according to Embodiment 1 of the present invention.

FIG. 1 illustrates a configuration of an ultrasound diagnostic apparatus 1 according to Embodiment 1 of the present invention. The ultrasound diagnostic apparatus 1 comprises an ultrasound probe 2 and an apparatus body 3 connected to the ultrasound probe 2.

The ultrasound probe 2 comprises a transducer array 11. A transmission and reception circuit 12 is connected to the transducer array 11.

The apparatus body 3 comprises an image generation unit 13. The image generation unit 13 is connected to the transmission and reception circuit 12 of the ultrasound probe 2. In addition, a display control unit 14 and a monitor 15 are sequentially connected to the image generation unit 13. In addition, a schema image generation unit 16 is connected to the image generation unit 13. In addition, a display control unit 14 and a text information conversion unit 17 are connected to the schema image generation unit 16. In addition, the apparatus body 3 comprises an external communication circuit 23 connected to an external apparatus, not illustrated. The text information conversion unit 17 is connected to the external communication circuit 23. In addition, a tag generation unit 24, a text information storage unit 18, and an image memory 19 are sequentially connected to the text information conversion unit 17.

In addition, an apparatus control unit 20 is connected to the transmission and reception circuit 12, the image generation unit 13, the display control unit 14, the schema image generation unit 16, the text information conversion unit 17, the text information storage unit 18, the image memory 19, the external communication circuit 23, and the tag generation unit 24. In addition, an input device 21 is connected to the apparatus control unit 20.

In addition, a processor 22 for the ultrasound diagnostic apparatus 1 is composed of the image generation unit 13, the display control unit 14, the schema image generation unit 16, the text information conversion unit 17, the text information storage unit 18, the apparatus control unit 20, and the tag generation unit 24 of the apparatus body 3.

The transducer array 11 of the ultrasound probe 2 includes a plurality of one-dimensionally or two-dimensionally arranged ultrasound oscillators. Each of these ultrasound oscillators transmits an ultrasound wave in accordance with a drive signal supplied from the transmission and reception circuit 12 and receives an ultrasound echo from a subject to output a signal based on the ultrasound echo. Each ultrasound oscillator is configured by forming electrodes at both ends of a piezoelectric body consisting of, for example, a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 2:
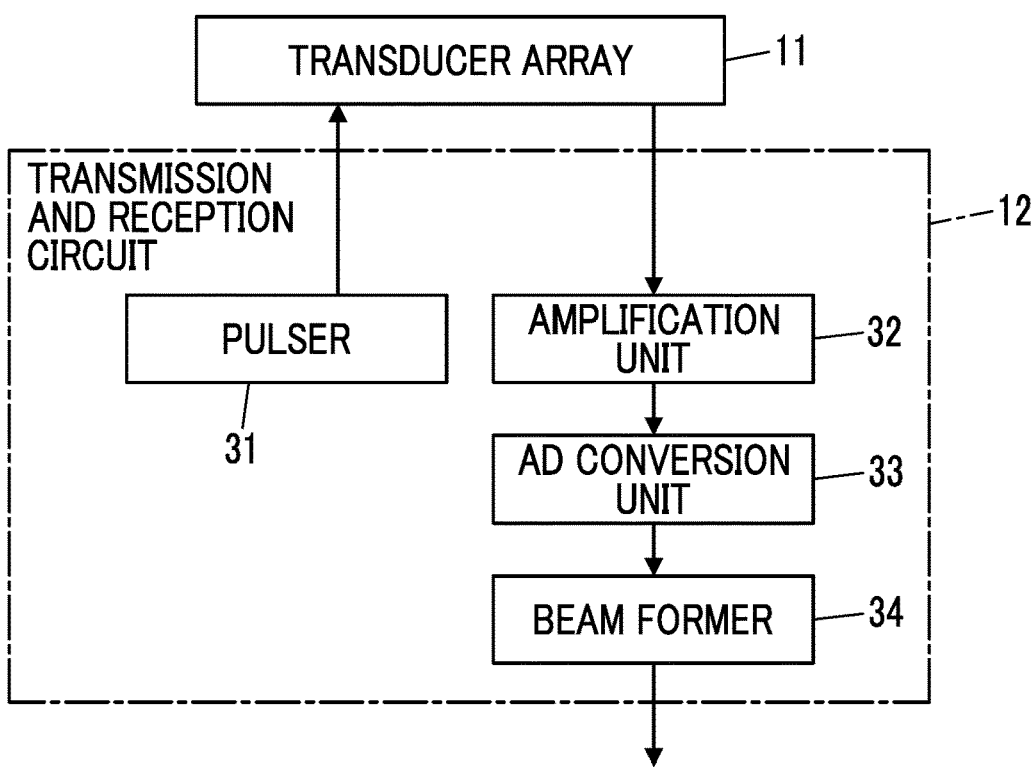
FIG. 2 is a block diagram illustrating a configuration of a transmission and reception circuit in Embodiment 1 of the present invention.

The transmission and reception circuit 12 transmits the ultrasound wave from the transducer array 11 and generates a sound ray signal based on a reception signal acquired by the transducer array 11 under control of the apparatus control unit 20. As illustrated in FIG. 2, the transmission and reception circuit 12 includes a pulser 31 connected to the transducer array 11 and an amplification unit 32, an analog digital (AD) conversion unit 33, and a beam former 34 sequentially connected in series from the transducer array 11.

The pulser 31 includes, for example, a plurality of pulse generators, adjusts a delay amount of each drive signal based on a transmission delay pattern selected in accordance with a control signal from the apparatus control unit 20 so that the ultrasound waves transmitted from the plurality of ultrasound oscillators of the transducer array 11 form an ultrasound beam, and supplies each drive signal to the plurality of ultrasound oscillators. In a case where a voltage having a pulse shape or a continuous wave shape is applied to the electrodes of the ultrasound oscillators of the transducer array 11, the piezoelectric bodies expand and contract to generate ultrasound waves having a pulse shape or a continuous wave shape from each ultrasound oscillator, and the ultrasound beam is formed from a combined wave of the ultrasound waves.

The transmitted ultrasound beam is reflected by, for example, a target such as a part of the subject and propagates toward the transducer array 11 of the ultrasound probe 2. The ultrasound echo propagating toward the transducer array 11 is received by each ultrasound oscillator constituting the transducer array 11. In this case, each ultrasound oscillator constituting the transducer array 11 receives the propagating ultrasound echo, expands and contracts to generate the reception signal that is an electric signal, and outputs the reception signal to the amplification unit 32.

The amplification unit 32 amplifies the signals input from each ultrasound oscillator constituting the transducer array 11 and transmits the amplified signals to the AD conversion unit 33. The AD conversion unit 33 converts the signals transmitted from the amplification unit 32 into digital reception data. The beam former 34 performs so-called reception focus processing of applying a delay to each reception data received from the AD conversion unit 33 and of adding each reception data together. By performing the reception focus processing, the sound ray signal in which each reception data converted by the AD conversion unit 33 is phased and added together and in which a focus of the ultrasound echo is narrowed is acquired.

Figure 3:
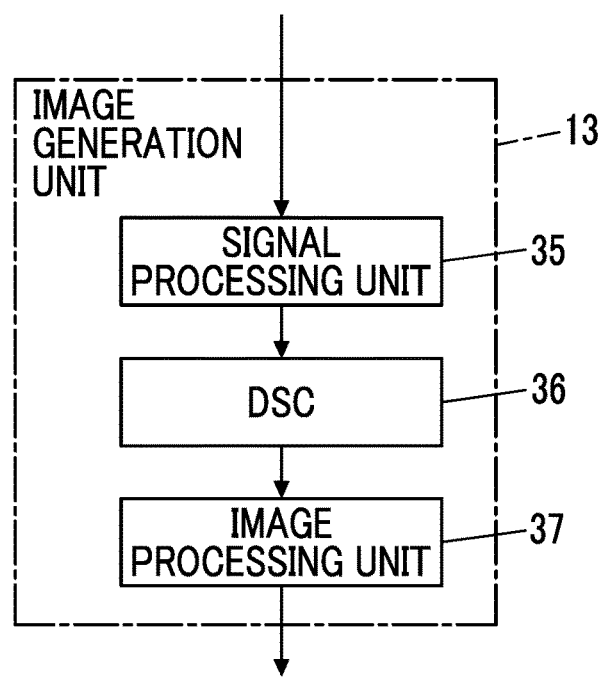
FIG. 3 is a block diagram illustrating a configuration of an image generation unit in Embodiment 1 of the present invention.

The image generation unit 13 has a configuration in which a signal processing unit 35, a digital scan converter (DSC) 36, and an image processing unit 37 are sequentially connected in series as illustrated in FIG. 3.

The signal processing unit 35 corrects attenuation by distance of the sound ray signal received from the transmission and reception circuit 12 in accordance with depths of reflection positions of the ultrasound waves using a sound speed value set by the apparatus control unit and then performs envelope detection processing on the sound ray signal to generate a B-mode image signal that is tomographic image information related to tissues inside the subject.

The DSC 36 converts the B-mode image signal generated by the signal processing unit 35 into an image signal complying with a scanning method of a typical television signal (raster conversion).

The image processing unit 37 performs various types of necessary image processing such as gradation processing on the B-mode image signal input from the DSC 36 and then transmits the B-mode image signal to the display control unit 14 and to the schema image generation unit 16. Hereinafter, the B-mode image signal on which the image processing is performed by the image processing unit 37 will be referred to as an ultrasound image.

The apparatus control unit 20 controls each part of the ultrasound probe 2 and each part of the apparatus body 3 in accordance with a program and the like recorded in advance.

The display control unit 14 performs predetermined processing on the ultrasound image or the like generated by the image generation unit 13 and displays the ultrasound image or the like on the monitor 15 under the control of the apparatus control unit 20.

The monitor 15 performs various types of display under control of the display control unit 14. Examples of the monitor 15 include display devices such as a liquid crystal display (LCD) and an organic electroluminescence display (organic EL display).

The input device 21 is used for a user to perform an input operation. For example, the input device 21 is composed of a device used for the user to perform the input operation, such as a keyboard, a mouse, a trackball, a touchpad, and a touch panel.

The external communication circuit 23 communicates with the external apparatus such as an external ultrasound diagnostic apparatus, an external storage device, or an external server apparatus, not illustrated, and acquires an ultrasound image U2 from the external apparatus under control of the apparatus control unit 20. The external communication circuit 23 can perform so-called wired communication or wireless communication with the external apparatus, not illustrated.

Figure 4:
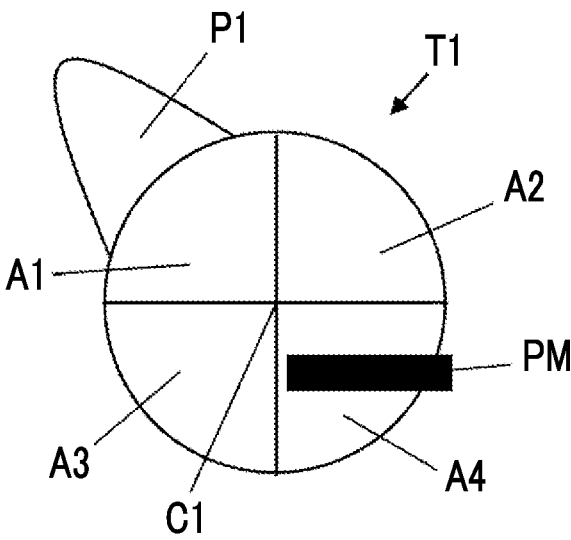
FIG. 4 is a diagram illustrating an example of a breast schema image generated in Embodiment 1 of the present invention.

The schema image generation unit 16 generates, for example, a so-called breast schema image T1 illustrated in FIG. 4.

The breast schema image T1 is an image schematically representing a breast of the subject and has a protrusion P1 representing an armpit of the subject and four regions A1 to A4 corresponding to quadrant regions of the breast of the subject with respect to a nipple as a center in a front view. The protrusion P1 is positioned on a left side in a front view of the breast schema image T1. Thus, the breast schema image T1 represents a right breast of the subject in a front view.

In addition, the region A1 corresponds to a region of a so-called upper outer quadrant (UOQ) on an upper outer side with respect to the nipple as a center. The region A2 corresponds to a region of a so-called upper inner quadrant (UIQ) on an upper inner side with respect to the nipple as a center. The region A3 corresponds to a region of a so-called lower outer quadrant (LOQ) on a lower outer side with respect to the nipple as a center. The region A4 corresponds to a region of a so-called lower inner quadrant (LIQ) on a lower inner side with respect to the nipple as a center.

While illustration is not provided, the schema image generation unit 16 can also generate a breast schema image representing a left breast in a front view of the subject, in which the protrusion P1 is positioned on a right side in a front view.

In addition, the schema image generation unit 16 positions a probe mark PM representing the ultrasound probe 2 in any of the four regions A1 to A4 of the breast schema image T1 based on a position of the ultrasound probe 2 that is plotted on the breast schema image T1 by the user through the input device 21.

Figure 5:
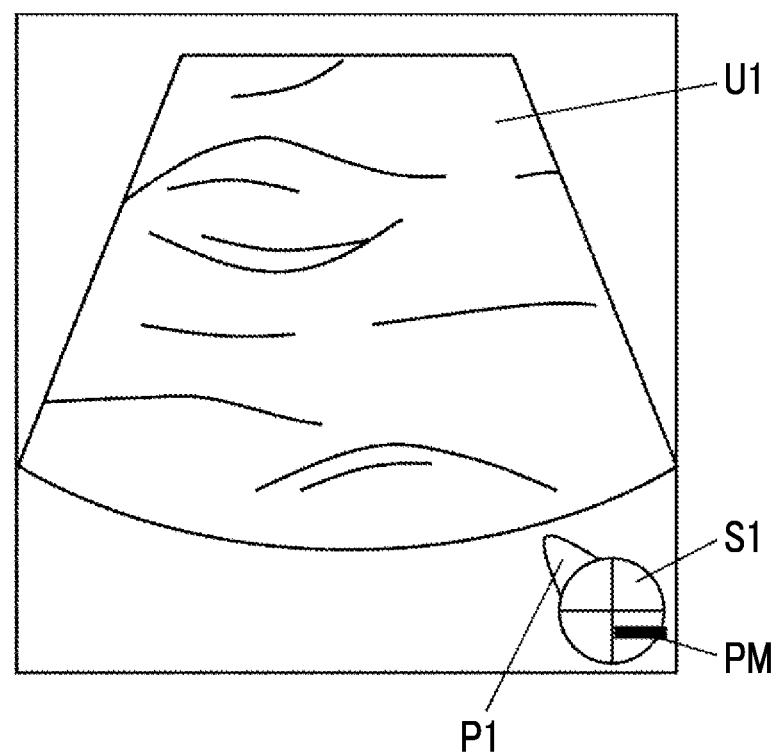
FIG. 5 is a diagram illustrating an example of an ultrasound image read in Embodiment 1 of the present invention.

Furthermore, for example, as illustrated in FIG. 5, the schema image generation unit 16 superimposes the breast schema image T1 including the probe mark PM on the ultrasound image U1 generated by the image generation unit 13 and transmits the ultrasound image U1 on which the breast schema image T1 is superimposed to the text information conversion unit 17.

In addition, the schema image generation unit 16 transmits the ultrasound image U1 on which the breast schema image T1 is superimposed to the display control unit 14 to display the ultrasound image U1 on the monitor 15 in accordance with an instruction from the apparatus control unit 20.

In addition, the schema image generation unit 16 transmits, to the text information conversion unit 17, information about the position of the ultrasound probe 2 that is plotted on the breast schema image T1 by the user through the input device 21.

Here, for example, information about coordinates of a position designated by the user with reference to coordinates of a center point C1 of the breast schema image T1 corresponding to the nipple can be used as the information about the position of the ultrasound probe 2 on the breast schema image T1.

The text information conversion unit 17 converts the position of the ultrasound probe 2 plotted on the breast schema image T1 into text information. For example, the text information conversion unit 17 can convert a region to which a plotted point in a case where the user plots the position of the ultrasound probe 2 on the breast schema image T1 through the input device 21 belongs among the four regions A1 to A4 of the breast schema image T1, into text information as the position of the ultrasound probe 2. For example, as illustrated in FIG. 4, in a case where the plotted point is plotted on the region A4 by the user and where the probe mark PM is positioned on the region A4, the text information conversion unit 17 can convert the position of the ultrasound probe 2 into a text "LIQ" that is a region on the breast of the subject corresponding to the region A4.

The tag generation unit 24 generates a tag of the ultrasound image U1 on which the breast schema image T1 is superimposed. For example, the tag generation unit 24 can generate a tag of the so-called Digital Imaging and Communications in Medicine (DICOM) standard as the tag of the ultrasound image U1.

The text information storage unit 18 stores the text information converted by the text information conversion unit 17 in the tag that is generated by the tag generation unit 24 and that is attached to the ultrasound image U1. In addition, the text information storage unit 18 stores, in the image memory 19, the ultrasound image U1 having the tag in which the text information is stored.

The image memory 19 stores the ultrasound image U1. The ultrasound image U1, stored in the image memory 19, on which the breast schema image T1 is superimposed and that has the tag in which the text information representing the position of the ultrasound probe 2 is stored can be read out based on an instruction from the apparatus control unit 20.

For example, recording media such as a flash memory, a hard disk drive (HDD), a solid state drive (SSD), a flexible disk (FD), a magneto-optical disc (MO disc), a magnetic tape (MT), a random access memory (RAM), a compact disc (CD), a digital versatile disc (DVD), a secure digital card (SD card), and a universal serial bus memory (USB memory) can be used as the image memory 19.

While the processor 22 including the image generation unit 13, the display control unit 14, the schema image generation unit 16, the text information conversion unit 17, the text information storage unit 18, the apparatus control unit 20, and the tag generation unit 24 is composed of a central processing unit (CPU) and of a control program causing the CPU to perform various types of processing, the processor 22 may be configured using a field programmable gate array (FPGA), a digital signal processor (DSP), an application specific integrated circuit (ASIC), a graphics processing unit (GPU), or other integrated circuits (IC) or may be composed of a combination thereof.

In addition, all or a part of the image generation unit 13, the display control unit 14, the schema image generation unit 16, the text information conversion unit 17, the text information storage unit 18, the apparatus control unit 20, and the tag generation unit 24 of the processor 22 can be configured to be integrated into one CPU or the like.

Next, operation of the ultrasound diagnostic apparatus 1 according to Embodiment 1 of the present invention will be described using the flowchart illustrated in FIG. 6.

First, the user positions the ultrasound probe 2 on the breast of the subject. In this state, the ultrasound image U1 is captured in step S1. In capturing the ultrasound image U1, the transmission and reception circuit 12 generates the sound ray signal by performing the so-called reception focus processing under control of the apparatus control unit 20. The sound ray signal generated by the transmission and reception circuit 12 is transmitted to the image generation unit 13. The image generation unit 13 generates the ultrasound image U1 using the sound ray signal transmitted from the transmission and reception circuit 12. The ultrasound image U1 generated in such a manner is transmitted to the display control unit 14 to be displayed on the monitor 15.

Next, in step S2, the apparatus control unit 20 determines whether or not the ultrasound image U1 displayed on the monitor 15 is frozen. Here, freezing the ultrasound image U1 means displaying only the ultrasound image U1 of one frame on the monitor 15 as a still image in accordance with an instruction of the user provided through the input device 21 in a state where the ultrasound image U1 that is continuously generated is being sequentially displayed on the monitor 15 as a video. In this case, for example, the ultrasound image U1 of one frame displayed at a timing at which the user provides a freeze instruction through the input device 21 is displayed on the monitor 15 as a still image.

In a case where it is determined that the ultrasound image U1 is not frozen in step S2, a return is made to step S1 to newly generate the ultrasound image U1 and display the ultrasound image U1 on the monitor 15. Thus, step S1 and step S2 are repeated as long as it is determined that the ultrasound image U1 is not frozen in step S2.

In a case where it is determined that the ultrasound image U1 is frozen in step S2, a transition is made to step S3.

In step S3, the schema image generation unit 16 generates the breast schema image T1. In this case, the breast schema image T1 is displayed on the monitor 15, and the user plots the position of the ultrasound probe 2 on the breast schema image T1 displayed on the monitor 15 through the input device 21. The schema image generation unit 16 positions the probe mark PM at a position of the plotted point plotted by the user and, for example, as illustrated in FIG. 5, superimposes, on the ultrasound image U1 frozen in step S2, the breast schema image T1 on which the probe mark PM is positioned.

In addition, the schema image generation unit 16 transmits the ultrasound image U1 on which the breast schema image T1 is superimposed to the text information conversion unit 17 and transmits information about the position of the plotted point plotted by the user to the text information conversion unit 17 as the information about the position of the ultrasound probe 2. Here, for example, information about coordinates of the plotted point on the breast schema image T1 with reference to a position of the center point C1 of the breast schema image T1 may be used as the information about the position of the plotted point.

In step S4, the apparatus control unit 20 determines whether or not to generate the tag to be attached to the ultrasound image U1 frozen in step S2. For example, the apparatus control unit 20 can display a message for asking whether or not to generate the tag of the ultrasound image U1 on the monitor 15 and, in a case where the user provides an instruction to generate the tag through the input device 21, determine to generate the tag. In addition, in a case where the user provides an instruction to not generate the tag through the input device 21, the apparatus control unit 20 can determine not to generate the tag.

For example, a message such as "Generate tag?" or "Store ultrasound image in DICOM standard?" may be displayed on the monitor 15 as the message for asking whether or not to generate the tag of the ultrasound image U1.

In step S4, in a case where it is determined to generate the tag of the ultrasound image U1, a transition is made to step S5.

In step S5, the text information conversion unit 17 converts the information about the position of the ultrasound probe 2 plotted on the breast schema image T1 into text information. For example, as illustrated in FIG. 4, in a case where the plotted point is plotted on the region A4 by the user and where the probe mark PM is positioned on the region A4, the text information conversion unit 17 can convert the position of the ultrasound probe 2 into the text "LIQ" that is the region on the breast of the subject corresponding to the region A4, by referring to the information about the coordinates of the plotted point generated in step S3.

Next, in step S6, the tag generation unit 24 generates the tag to be attached to the ultrasound image U1 frozen in step S2. For example, the tag generation unit 24 can generate the tag in the DICOM standard.

Next, in step S7, the text information storage unit 18 stores the text information converted in step S5 in the tag of the ultrasound image U1 generated in step S6.

Last, in step S8, the ultrasound image U1 having the tag in which the text information is stored in step S7 is stored in the image memory 19. In this case, for example, the user providing an instruction to store the ultrasound image U1 through the input device 21 triggers storage of the ultrasound image U1 in the image memory 19 under control of the apparatus control unit 20.

In addition, in a case where it is determined not to generate the tag in step S4, a transition is made to step S8 without performing step S5 to step S7.

In step S8, the ultrasound image U1 that is frozen in step S2 and on which the breast schema image T1 is superimposed in step S3 is stored in the image memory 19.

Figure 6:
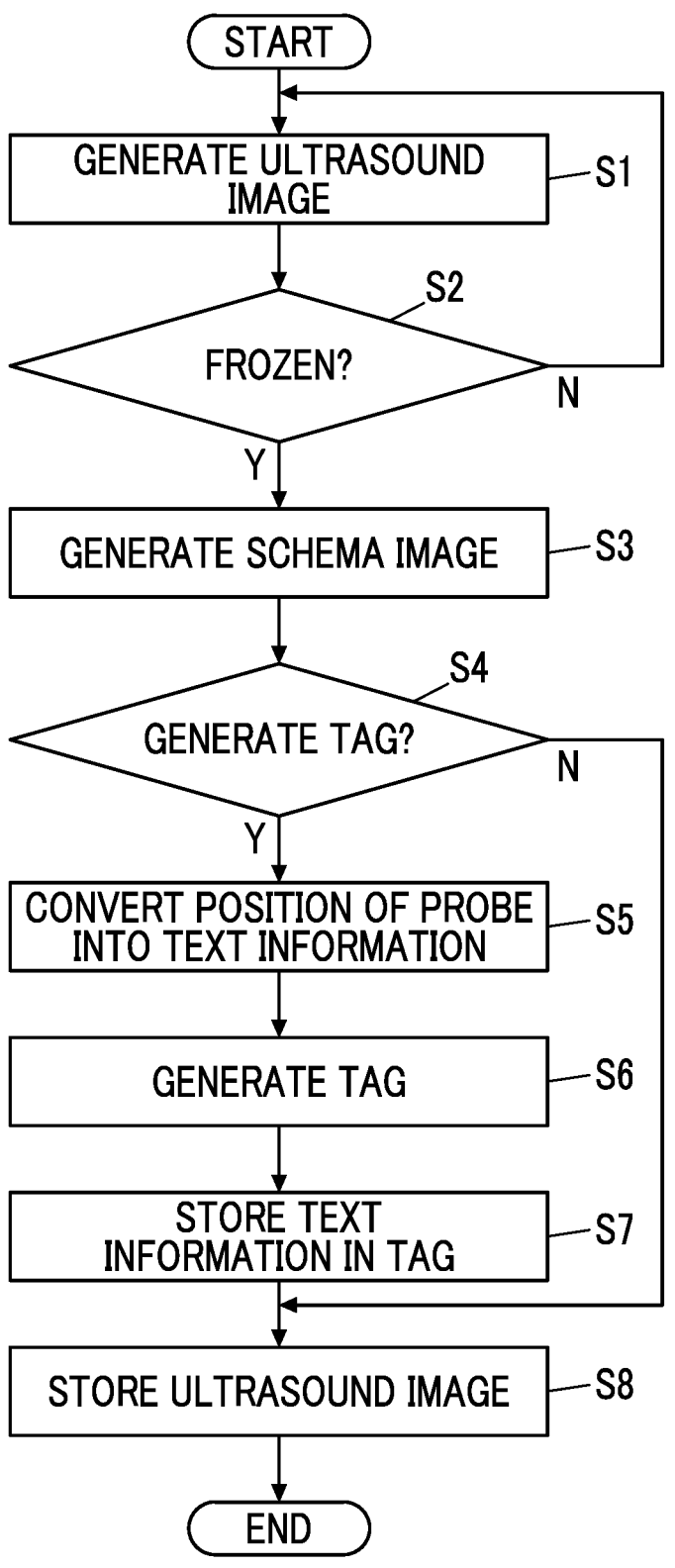
FIG. 6 is a flowchart illustrating operation of the ultrasound diagnostic apparatus according to Embodiment 1 of the present invention.

In a case where processing of step S8 is completed, the operation of the ultrasound diagnostic apparatus 1 illustrated in the flowchart of FIG. 6 ends.

As illustrated in FIG. 4, displaying the ultrasound image U1 on which the breast schema image T1 is superimposed on the monitor 15 enables the user to visually perceive the position of the ultrasound probe 2 in a case where the ultrasound image U1 is captured. However, for example, each time the position of the ultrasound probe 2 visually shown by the breast schema image T1 is read via mechanical processing, certain processing is required.

According to the ultrasound diagnostic apparatus 1 according to Embodiment 1 of the present invention, the information about the position of the ultrasound probe 2 on the breast schema image T1 designated by the user through the input device 21 is converted into the text information and is stored in the tag of the ultrasound image U1. Thus, the information about the position of the ultrasound probe 2 in a case where the ultrasound image U1 is captured can be read out from the tag of the ultrasound image U1 as the text information. Accordingly, for example, it is easy to automatically write the information about the position of the ultrasound probe 2 on a report or the like as a text, and the user can easily use the information stored in the tag of the ultrasound image U1.

While the position of the ultrasound probe 2 on the breast schema image T1 has been described as being plotted by the user through the input device 21 in step S3, the position of the ultrasound probe 2 on the breast schema image T1 may be plotted by the user at a timing at which, for example, examination of the subject is started.

In addition, in step S3 or at the timing at which examination of the subject is started, the apparatus control unit 20 can display, on the monitor 15, a message for prompting the user to plot the position of the ultrasound probe 2 on the breast schema image T1. Accordingly, the user can securely plot the position of the ultrasound probe 2 on the breast schema image T1.

In addition, while an example of determining whether or not to generate the tag in accordance with an instruction of the user provided through the input device 21 in step S4 has been described, a method of determining whether or not to generate the tag is not limited thereto. For example, the apparatus control unit 20 can set whether to store the ultrasound image U1 in the form of not attaching the tag or store the ultrasound image U1 in the form of attaching the tag in advance in accordance with an instruction of the user provided through the input device 21 and determine whether or not to generate the tag based on the form of storage of the ultrasound image U1 set in advance without asking the user whether or not to generate the tag of the ultrasound image U1.

In addition, while the text information conversion unit 17 converts the information about the position of the plotted point on the breast schema image T1 input by the user in step S3 into the text information in step S5, it is possible to, for example, recognize the position of the plotted point on the breast schema image T1 by performing image analysis on the breast schema image T1 and to convert the information about the recognized position of the plotted point into the text information.

Figure 7:
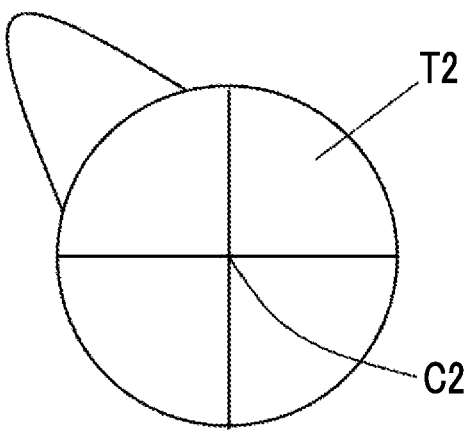
FIG. 7 is a diagram illustrating an example of a template of a breast schema used in Embodiment 1 of the present invention.

In this case, for example, the text information conversion unit 17 extracts the probe mark PM representing the position of the ultrasound probe 2 from the breast schema image T1 by calculating a difference between the breast schema image T1 on which the probe mark PM is positioned as illustrated in FIG. 4 and a template T2 of the breast schema on which the probe mark PM is not positioned as illustrated in FIG. 7, and calculates coordinates of a center of the probe mark PM with reference to a position of a center point C2 of the template T2 of the breast schema. Furthermore, the text information conversion unit 17 can convert a region to which the probe mark PM belongs among the four regions A1 to A4 into the text information as the position of the ultrasound probe 2 by referring to the calculated coordinates of the center of the probe mark PM.

In addition, while examples of the text information obtained by the text information conversion unit 17 include "UOQ", "UIQ", "LOQ", and "LIQ" representing the regions of the breast of the subject, the text information may be, for example, a string of numbers or any character string set by the user.

In addition, while the breast schema image T1 divided into four regions of UOQ, UIQ, LOQ, and LIQ with respect to the nipple as a center in a front view of each of the left and right breasts of the subject has been illustrated, the type of breast schema image T1 is not particularly limited thereto. In the present invention, while illustration is not provided, for example, a breast schema image divided into a center region in which the nipple is positioned and into regions corresponding to directions of 1 o'clock to 12 o'clock of a timepiece with respect to the nipple as a center in a front view of the left or right breast of the subject, a breast schema image that is concentrically divided with respect to the nipple as a center in a front view of the left or right breast of the subject or that is divided by a plurality of contour lines with respect to the nipple as an apex part in a side view of the left or right breast of the subject, or the like can be used.

While the ultrasound image U1 is stored in the image memory 19 in step S8, the ultrasound image U1, instead, can be transmitted to the external apparatus, not illustrated, through the external communication circuit 23. Even in this case, the user can easily use the information stored in the tag of the ultrasound image U1 by using the ultrasound image U1 transmitted to the external apparatus.

In addition, the ultrasound image U2 on which the breast schema image T1 is superimposed may be input into the ultrasound diagnostic apparatus 1 from the external apparatus such as an external ultrasound diagnostic apparatus, not illustrated, or an external server apparatus, not illustrated. The ultrasound image U2 input from the external apparatus in such a manner is transmitted to the display control unit 14 to be displayed on the monitor 15 under control of the apparatus control unit 20.

In addition, in a case where the ultrasound image U2 is input from the external apparatus, not illustrated, through the external communication circuit 23, step S1 in which the ultrasound image U1 is generated, step S2 in which whether or not the ultrasound image U1 is frozen is determined, and step S3 in which the breast schema image T1 is generated in the flowchart of FIG. 6 are replaced with a step of acquiring the ultrasound image U2. Subsequent step S4 to step S8 are identical.

In this case, in a case where the information about the position of the ultrasound probe 2 on the breast schema image T1 is attached to the ultrasound image U2 input from the external apparatus, not illustrated, through the external communication circuit 23, the text information conversion unit 17 can convert the information about the position of the ultrasound probe 2 on the breast schema image T1 attached to the received ultrasound image U2 into the text information in step S5.

In addition, in step S5, the text information conversion unit 17 can recognize the position of the ultrasound probe 2 on the breast schema image T1 by performing image analysis on the ultrasound image U2 that is input from the external apparatus through the external communication circuit 23 and on which the breast schema image T1 is superimposed, and convert the information about the recognized position of the ultrasound probe 2 into the text information.

In addition, in a case where an ultrasound image on which the breast schema image T1 is superimposed and to which the tag is not attached is stored in the image memory 19, the text information conversion unit 17 can recognize the position of the ultrasound probe 2 on the breast schema image T1 superimposed on the ultrasound image by reading out the ultrasound image to which the tag is not attached from the image memory 19 and by performing image analysis on the ultrasound image, and convert the information about the recognized position of the ultrasound probe 2 into the text information in the same manner as the ultrasound image U2 input from the external apparatus, not illustrated, through the external communication circuit 23.

Embodiment 2

In Embodiment 1, the breast schema image T1 generated by the schema image generation unit 16 is superimposed on the ultrasound image U1 generated by the image generation unit 13, and the ultrasound image U1 on which the breast schema image T1 is superimposed is stored in the image memory 19. Instead, a captured image obtained by capturing a screen display of the monitor 15 on which the ultrasound image U1 is displayed may be stored in the image memory 19 as an ultrasound image. Here, capturing means obtaining an image by cutting out the screen display of the monitor 15 using a method of a so-called screenshot, screen capturing, a screen dump, or the like.

Figure 8:
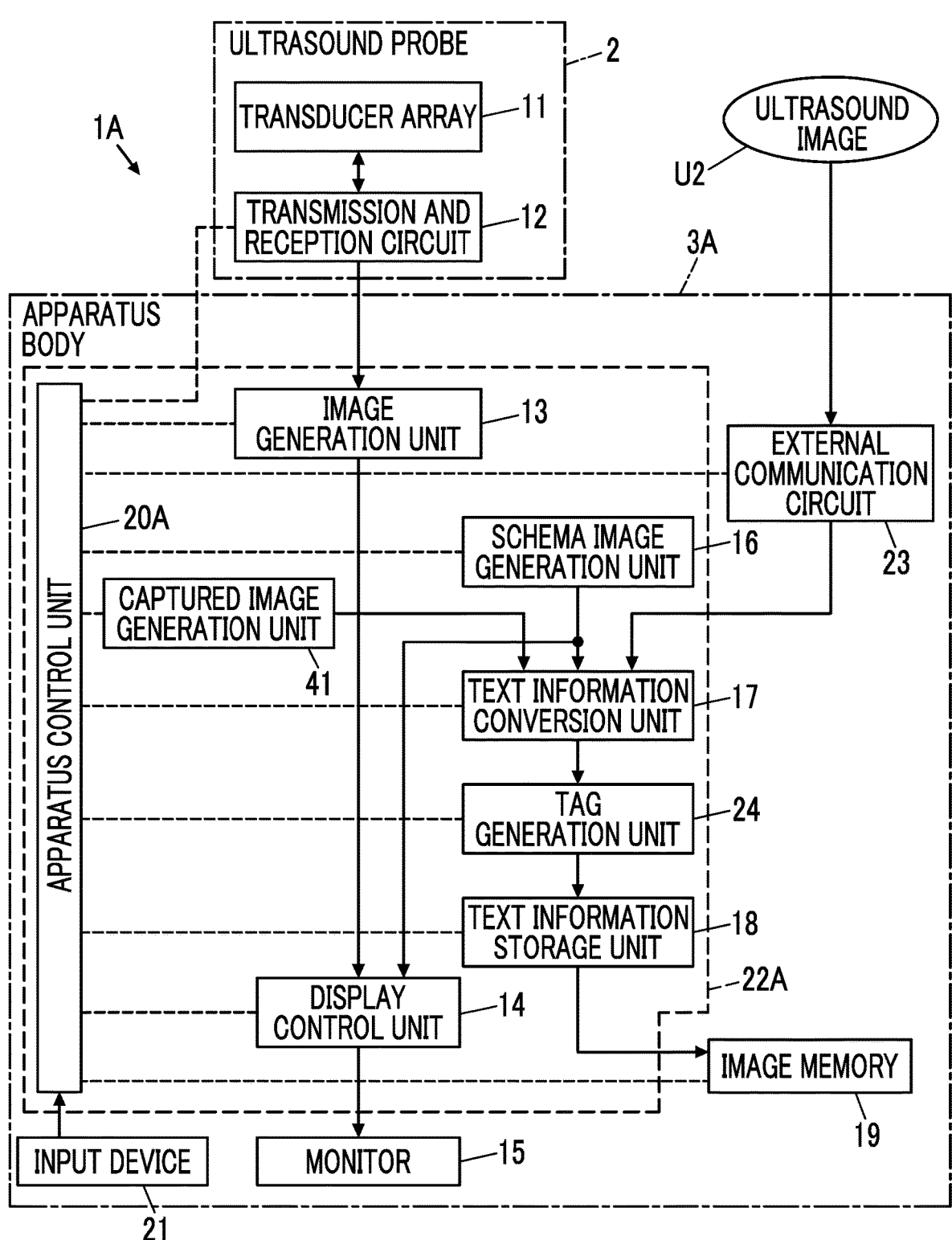
FIG. 8 is a block diagram illustrating a configuration of an ultrasound diagnostic apparatus according to Embodiment 2 of the present invention.

FIG. 8 illustrates a configuration of an ultrasound diagnostic apparatus 1A according to Embodiment 2 of the present invention. The ultrasound diagnostic apparatus 1A comprises an apparatus body 3A instead of the apparatus body 3 in the ultrasound diagnostic apparatus 1 of Embodiment 1 illustrated in FIG. 1.

The apparatus body 3A includes a captured image generation unit 41 added to the apparatus body 3 in Embodiment 1, comprises an apparatus control unit 20A instead of the apparatus control unit 20, and comprises a processor 22A instead of the processor 22.

In Embodiment 2, the schema image generation unit 16 is connected to the display control unit 14, the text information conversion unit 17, and the apparatus control unit 20A. In addition, the external communication circuit 23 is connected to the text information conversion unit 17 and to the apparatus control unit 20A. In addition, the captured image generation unit 41 is connected to the text information conversion unit 17 and to the apparatus control unit 20A.

In addition, the processor 22A is composed of the image generation unit 13, the display control unit 14, the schema image generation unit 16, the text information conversion unit 17, the text information storage unit 18, the apparatus control unit 20A, the tag generation unit 24, and the captured image generation unit 41.

The captured image generation unit 41 generates the captured image by cutting out the screen display of the monitor 15 on which the ultrasound image U1 and the breast schema image T1 are displayed, using a method of a so-called screenshot, screen capturing, a screen dump, or the like under control of the apparatus control unit 20A.

The text information conversion unit 17 converts the position of the ultrasound probe 2 plotted on the breast schema image T1 into the text information in the same manner as Embodiment 1.

The tag generation unit 24 generates a tag of the captured image including the ultrasound image U1 on which the breast schema image T1 is superimposed in the same manner as Embodiment 1.

The text information storage unit 18 stores the text information converted by the text information conversion unit 17 in the tag that is generated by the tag generation unit 24 and that is attached to the captured image. In addition, the text information storage unit 18 stores, in the image memory 19, the captured image having the tag in which the text information is stored as an ultrasound image.

Next, operation of the ultrasound diagnostic apparatus 1A of Embodiment 2 will be described using the flowchart of FIG. 9. The flowchart of FIG. 9 includes step S11 to step S18 replacing step S1 to step S3 and step S19 replacing step S8 in the flowchart of FIG. 6.

First, in step S11, the ultrasound image U1 is generated in the same manner as step S1 in the flowchart of FIG. 6.

In step S12, the schema image generation unit 16 generates a breast schema image. In the breast schema image generated in this case, the probe mark PM showing the position of the ultrasound probe 2 in the breast schema image T1 illustrated in FIG. 4 is removed.

In step S13, the breast schema image generated in step S12 is superimposed on the ultrasound image U1 generated in step S11, and the ultrasound image U1 is displayed on the monitor 15.

Next, in step S14, the apparatus control unit 20A determines whether or not the ultrasound image U1 displayed on the monitor 15 is frozen in the same manner as step S2 in Embodiment 1.

In a case where it is determined that the ultrasound image U1 is not frozen in step S14, a return is made to step S11 to newly generate the ultrasound image U1, and processing of step S12, step S13, and step S14 is sequentially performed. Thus, processing of step S11 to step S14 is repeated until it is determined that the ultrasound image U1 is frozen in step S14.

In a case where it is determined that the ultrasound image U1 is frozen in step S14, a transition is made to step S15.

In step S15, the apparatus control unit 20A determines whether or not the position of the ultrasound probe 2 is confirmed. For example, in a case where the user designates a position on the breast schema image corresponding to the position of the ultrasound probe 2 through the input device 21 in a state where the ultrasound image U1 is frozen and where the ultrasound image U1 and the breast schema image not having the probe mark PM are displayed on the monitor 15, the apparatus control unit 20A determines that the position of the ultrasound probe 2 is confirmed. In addition, in a case where the instruction of the user is not input, processing of step S5 is repeated.

In a case where it is determined that the position of the ultrasound probe 2 is confirmed in step S15, a transition is made to step S16.

In step S16, the schema image generation unit 16 positions the probe mark PM at the position on the breast schema image designated by the user in step S15. Accordingly, the breast schema image T1 to which the probe mark PM is assigned as illustrated in FIG. 4 is obtained. In this case, the schema image generation unit 16 transmits information about the position on the breast schema image designated by the user in step S15 to the text information conversion unit 17.

In step S17, the ultrasound image U1 frozen in step S14 and the breast schema image T1 obtained in step S16 are displayed on the monitor 15.

In step S18, the captured image generation unit 41 generates the captured image by capturing the screen display of the monitor 15 in a state where the ultrasound image U1 and the breast schema image T1 are displayed on the monitor 15 in step S17. The captured image includes the ultrasound image U1 and the breast schema image T1.

In a case where processing of step S18 is completed in such a manner, a transition is made to step S4.

In step S4, the apparatus control unit 20A determines whether or not to generate the tag to be attached to the captured image generated in step S18. A determination method in this case is identical to the determination method described in step S4 in Embodiment 1.

In a case where it is determined to generate the tag in step S4, a transition is made to step S5.

In step S5, the text information conversion unit 17 converts the information about the position of the ultrasound probe 2 plotted on the breast schema image T1 into the text information.

In step S6, the tag generation unit 24 generates the tag to be attached to the captured image generated in step S18 as a tag to be attached to the ultrasound image.

In step S7, the text information storage unit 18 stores the text information converted in step S5 in the tag of the captured image generated in step S6.

Last, in step S19, the captured image having the tag in which the text information representing the position of the ultrasound probe 2 is stored is stored in the image memory 19.

In addition, in a case where it is determined not to generate the tag in step S4, a transition is made to step S19 to store the captured image to which the tag is not attached in the image memory 19.

Figure 9:
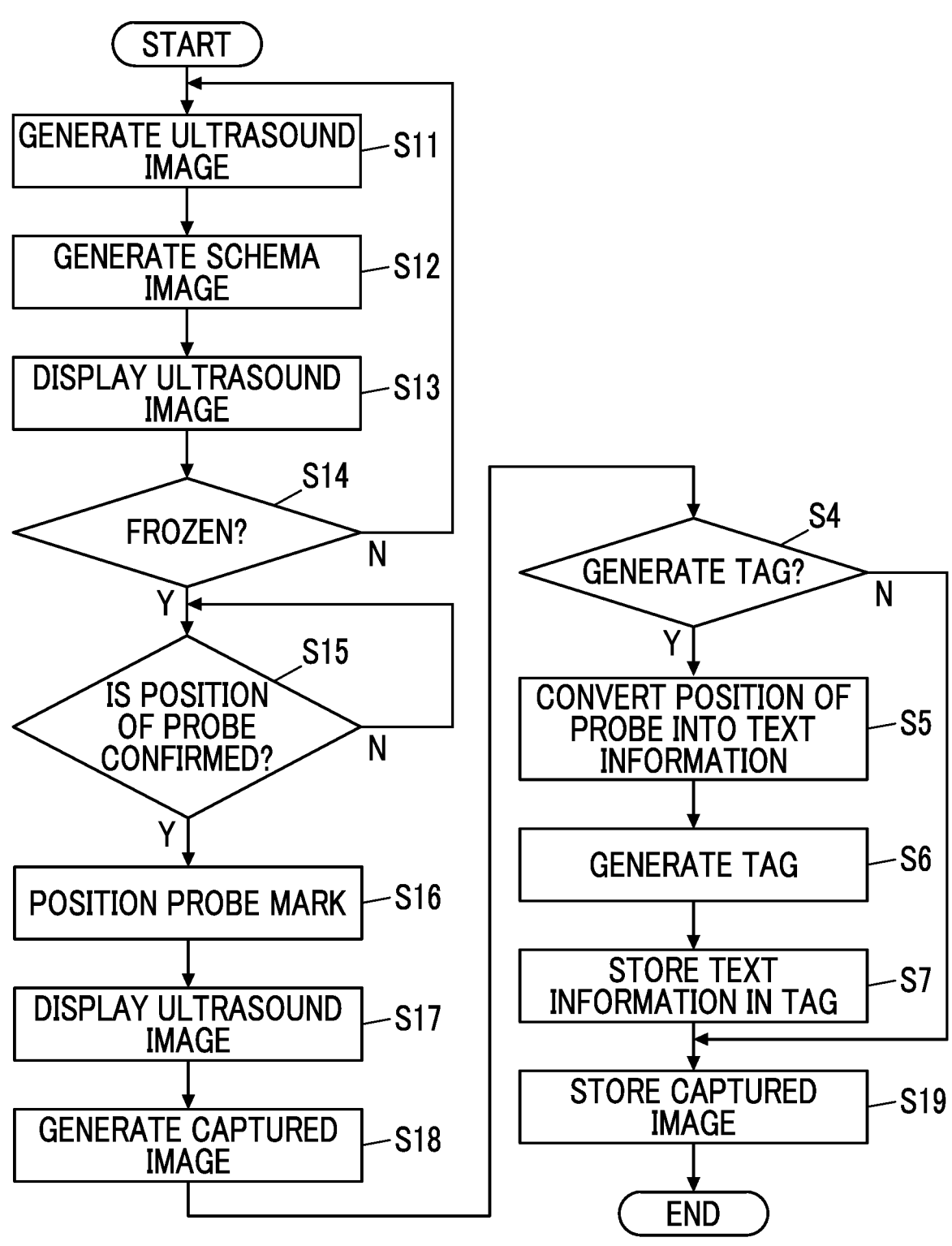
FIG. 9 is a flowchart illustrating operation of the ultrasound diagnostic apparatus according to Embodiment 2 of the present invention.

This ends the operation of the ultrasound diagnostic apparatus 1A according to the flowchart of FIG. 9.

As described above, even in a case where the captured image including the ultrasound image U1 and the breast schema image T1 is stored in the image memory 19 as an ultrasound image, the information about the position of the ultrasound probe 2 on the breast schema image T1 designated by the user through the input device 21 is converted into the text information and is stored in the tag of the captured image. Thus, the information about the position of the ultrasound probe 2 in a case where the ultrasound image U1 is captured can be read out from the tag as text information in the same manner as Embodiment 1. Accordingly, the user can easily use the information stored in the tag of the ultrasound image U1.

Aspects of Embodiment 2 may be combined with Embodiment 1 as appropriate.

EXPLANATION OF REFERENCES 1, 1A: ultrasound diagnostic apparatus
2: ultrasound probe
3, 3A: apparatus body
11: transducer array
12: transmission and reception circuit
13: image generation unit
14: display control unit
15: monitor
16: schema image generation unit
17: text information conversion unit
18: text information storage unit
19: image memory
20A: apparatus control unit
21: input device
22, 22A: processor
23: external communication circuit
24: tag generation unit
31: pulser
32: amplification unit
33: AD conversion unit
34: beam former
35 signal processing unit
36: DSC
37: image processing unit
41: captured image generation unit
A1 to A4: region
C1, C2: center point
P1: protrusion
PM: probe mark
T1: breast schema image
T2: template
U1, U2: ultrasound image

What is claimed is:

1. An ultrasound diagnostic apparatus that displays an ultrasound image on which a breast schema image showing a position of an ultrasound probe in imaging is superimposed, the apparatus comprising:

an external communication circuit configured to receive, from an external apparatus, the ultrasound image on which the breast schema image is superimposed; and a processor configured to convert the position of the ultrasound probe plotted on the breast schema image into text information representing one of a plurality of regions by which a breast of a subject is divided, by:

extracting, from the breast schema image superimposed on the ultrasound image received via the external communication circuit, a probe mark representing the position of the ultrasound probe by calculating a difference between the breast schema image and a template of a breast schema, calculating coordinates of a center of the probe mark with reference to a center point of the template, and converting a region to which the coordinates of the center of the probe mark belong among among the plurality of divided regions of the breast into the text information as the position of the ultrasound probe; and store the converted text information in a tag of the Digital Imaging and Communications in Medicine (DICOM) standard attached to the ultrasound image.

2. A control method of an ultrasound diagnostic apparatus that displays an ultrasound image on which a breast schema image showing a position of an ultrasound probe in imaging is superimposed, the method comprising:

receiving, from an external apparatus, the ultrasound image on which the breast schema image is superimposed;

converting the position of the ultrasound probe plotted on the breast schema image into text information representing one of a plurality of regions by which a breast of a subject is divided, by:

extracting, from the breast schema image superimposed on the ultrasound image received via the external communication circuit, a probe mark representing the position of the ultrasound probe by calculating a difference between the breast schema image and a template of a breast schema, calculating coordinates of a center of the probe mark with reference to a center point of the template, and converting a region to which the coordinates of the center of the probe mark belong among the plurality of divided regions of the breast into the text information as the position of the ultrasound probe; and storing the converted text information in a tag of the Digital Imaging and Communications in Medicine (DICOM) standard attached to the ultrasound image.

\* \* \* \* \*